United States Patent
Heimbecher

(10) Patent No.: US 8,708,902 B2
(45) Date of Patent: Apr. 29, 2014

(54) CATHETER CONFIGURATION INTERFACE AND RELATED SYSTEM

(75) Inventor: Reed R. Heimbecher, Hamel, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 524 days.

(21) Appl. No.: 12/982,562

(22) Filed: Dec. 30, 2010

(65) Prior Publication Data

US 2012/0173217 A1   Jul. 5, 2012

(51) Int. Cl.
*A61B 5/00* (2006.01)
*G06F 19/00* (2011.01)
*A61B 19/00* (2006.01)

(52) U.S. Cl.
CPC ............. *G06F 19/34* (2013.01); *A61B 19/5244* (2013.01)
USPC ........................................................ 600/300

(58) Field of Classification Search
USPC ................... 600/300–301; 606/130; 382/128; 604/67
See application file for complete search history.

(56) References Cited

U.S. PATENT DOCUMENTS

| | | | |
|---|---|---|---|
| 7,263,397 B2 | 8/2007 | Hauck et al. | |
| 7,386,339 B2 | 6/2008 | Strommer et al. | |
| 7,740,606 B2 * | 6/2010 | Hartlep et al. | 604/67 |
| 7,835,925 B2 * | 11/2010 | Roe et al. | 705/3 |
| 8,388,582 B2 * | 3/2013 | Eubanks et al. | 604/239 |
| 2001/0055413 A1 * | 12/2001 | Florent et al. | 382/128 |
| 2007/0249911 A1 * | 10/2007 | Simon | 600/300 |
| 2008/0015432 A1 * | 1/2008 | Hartlep et al. | 600/419 |
| 2008/0110460 A1 * | 5/2008 | Elaz et al. | 128/204.21 |
| 2008/0275467 A1 * | 11/2008 | Liao et al. | 606/130 |
| 2009/0124964 A1 * | 5/2009 | Leach et al. | 604/66 |
| 2009/0182226 A1 * | 7/2009 | Weitzner et al. | 600/424 |
| 2009/0247942 A1 | 10/2009 | Kirschenman | |
| 2009/0247944 A1 | 10/2009 | Kirschenman et al. | |
| 2009/0247993 A1 | 10/2009 | Kirschenman et al. | |
| 2009/0248042 A1 * | 10/2009 | Kirschenman | 606/130 |
| 2010/0130836 A1 * | 5/2010 | Malchano et al. | 600/301 |
| 2010/0210938 A1 * | 8/2010 | Verard et al. | 600/424 |
| 2010/0222647 A1 * | 9/2010 | Hashimshony et al. | 600/301 |
| 2010/0256558 A1 | 10/2010 | Olson et al. | |
| 2011/0002513 A1 * | 1/2011 | Molinari et al. | 382/128 |
| 2011/0015569 A1 | 1/2011 | Kirschenman et al. | |
| 2011/0028989 A1 * | 2/2011 | Ritter et al. | 606/130 |
| 2011/0060229 A1 * | 3/2011 | Hulvershorn et al. | 600/486 |
| 2011/0106004 A1 * | 5/2011 | Eubanks et al. | 604/35 |

(Continued)

FOREIGN PATENT DOCUMENTS

WO   WO 2009/0120982 A2   10/2009

*Primary Examiner* — Bill Thomson
*Assistant Examiner* — Bobby Soriano
(74) *Attorney, Agent, or Firm* — Dykema Gossett PLLC

(57) ABSTRACT

A system for implementing a procedure for the diagnosis or treatment of tissue in a body is provided. The system includes an electronic control unit configured to generate a graphical user interface on a display. The interface depicts an image of the tissue. The unit is further configured to receive one or more inputs regarding target locations on the tissue for diagnosis or treatment. The electronic control unit identifies a catheter for use in the procedure and determines configurations for a distal end of the catheter at each target location. The unit superimposes representations of the distal end of the catheter having the determined configurations on the image of the tissue at the target locations. The unit may also generate control signals to guide the distal end of the catheter to the target locations and to assume the determined configurations at each location.

21 Claims, 5 Drawing Sheets

(56) References Cited

U.S. PATENT DOCUMENTS

| | | | |
|---|---|---|---|
| 2011/0144657 A1* | 6/2011 | Fish et al. | 606/130 |
| 2011/0206256 A1* | 8/2011 | Ramanathan et al. | 382/128 |
| 2012/0014574 A1* | 1/2012 | Ferschel et al. | 382/128 |
| 2012/0230565 A1* | 9/2012 | Steinberg et al. | 382/130 |

* cited by examiner

CATHETER CONFIGURATION INTERFACE AND RELATED SYSTEM

BACKGROUND OF THE INVENTION a. Field of the Invention

This invention relates to a system for implementing a procedure for the diagnosis or treatment of tissue in a body. In particular, the instant invention relates to a system that permits more effective planning and implementation of medical procedures employing catheters.

b. Background Art

Catheters are used in numerous procedures for the diagnosis and/or treatment of tissues in the body. A variety of catheters may be used, for example, in the treatment of cardiac arrhythmias (including, but not limited to, atrial fibrillation, atrial flutter, atrial tachycardia, and ventricular tachycardia). Arrhythmia can create a variety of dangerous conditions including irregular heart rates, loss of synchronous atrioventricular contractions and stasis of blood flow, which can lead to a variety of ailments and even death. It is believed that the primary cause of many arrhythmias is stray electrical signals within one or more heart chambers. An ablation catheter imparts ablative energy (e.g., radiofrequency energy, light energy, ultrasound, or thermal (cryo or heat based) energy) to the heart tissue to create a lesion in the heart tissue. This lesion disrupts undesirable electrical pathways and thereby limits or prevents stray electrical signals that lead to arrhythmias. In addition to ablation catheters, electrophysiology (EP) catheters may be used to detect and map electrical activity in the heart while other catheters may be used to image cardiac tissue including intracardiac echocardiography (ICE) catheters.

When implementing procedures involving the use of catheters, it is desirable to minimize the time required for the procedure. Minimizing the time required for the procedure reduces risks to the patient from prolonged exposure to anesthesia and the presence of foreign objects within the body. Minimizing the time required for the procedure also reduces resource costs for health care providers and improves patient access to health care. Accordingly, medical procedures involving catheters are carefully planned to limit the time required and increase the effectiveness of the procedure.

Despite careful planning, the vagaries of patient anatomies and responses to external stimuli frequently create unexpected results. For example, a clinician may plan and/or attempt to implement a procedure by configuring a catheter in a certain way at a target location only to learn after arriving at the location that the patient's anatomy and/or limitations associated with the catheter prevent such a configuration. Further, the ability to optimally plan the procedure is often limited in conventional systems. In particular, it is often difficult to determine an optimal order for visiting multiple target locations for diagnosis and treatment. As a result, clinicians often default to a plan that involves moving the shortest distance among target locations. This order may not be optimized for achieving the desired diagnosis or treatment, however, resulting in unnecessarily prolonging procedures and, in the case of cardiac ablation, unnecessary lesions in the heart tissue.

The inventor herein has recognized a need for a system for implementing a procedure for the diagnosis or treatment of tissue in a body that will minimize and/or eliminate one or more of the above-identified deficiencies.

BRIEF SUMMARY OF THE INVENTION

It is desirable to provide a system for implementing a procedure for the diagnosis or treatment of tissue in a body. In particular, it is desirable to provide a system that permits more effective planning and implementation of medical procedures employing catheters.

A system for implementing a procedure for the diagnosis or treatment of tissue in a body in accordance with one embodiment of the invention includes an electronic control unit configured to generate a graphical user interface on a display. The graphical user interface depicts an image of the tissue. The electronic control unit is further configured to receive inputs regarding one or more target locations on the tissue. The electronic control unit is further configured to identify a catheter for use in the procedure. In one embodiment of the invention, the electronic control unit identifies the catheter by receiving identifying information from the catheter upon connection of the catheter to the electronic control unit. In another embodiment, the electronic control unit identifies the catheter by receiving an input through an input device connected to the electronic control unit such as the graphical user interface. The electronic control unit is further configured to determine a configuration for a distal end of the catheter at each of the target locations. In one embodiment of the invention, the electronic control unit determines the configuration by generating a plurality of potential configurations for the distal end of the catheter, displaying a plurality of icons on the graphical user interface with each icon of the plurality of icons corresponding to a potential configuration in at least a subset of the plurality of potential configurations, and recognizing a selected configuration from among the plurality of potential configurations as the configuration for the target location responsive to an input. In another embodiment, the control unit determines the configuration by selecting the configuration from among a plurality of potential configurations for the distal end of the catheter. The selection may, for example, be made by the control unit responsive to a characteristic associated with the tissue. The electronic control unit is further configured to superimpose a representation of the distal end of the catheter on the image of the tissue at the target location, wherein the representation depicts the distal end of the catheter in the configuration. In accordance with another embodiment of the invention, the electronic control unit is further configured to generate control signals to guide the distal end of the catheter to the target locations and to assume the determined configurations at each location.

A system in accordance with the present invention is advantageous because it permits a clinician to establish the configuration for the distal end of the catheter at each target location during planning for the procedure and to evaluate potential configurations relative to limitations in the patient's anatomy or in the catheter itself prior to inserting the catheter into the patient's body. The invention also allows for optimal ordering of actions in the procedure by the physician or the system itself. As a result, the time required to implement the procedure is minimized thereby reducing risks to the patient and resources required from health care providers.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Figure 1:
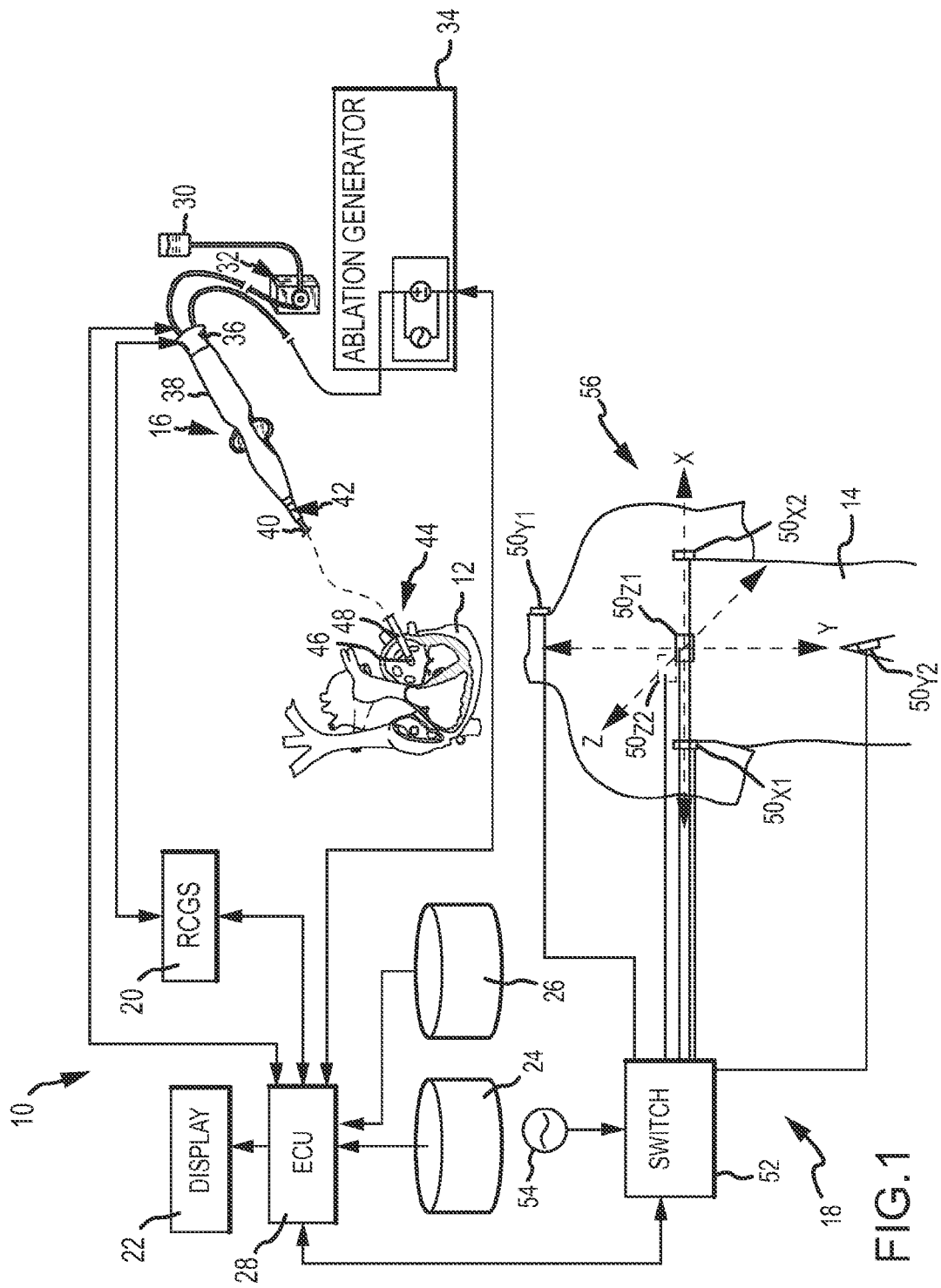
FIG. 1 is diagrammatic view of one embodiment of a system in accordance with the present teachings.

Referring now to the drawings wherein like reference numerals are used to identify identical components in the various views, FIG. 1 illustrates one embodiment of a system 10 for implementing a procedure for the diagnosis or treatment of tissue 12 in a body 14. In the illustrated embodiment, tissue 14 comprises cardiac tissue within a human body. It should be understood, however, that a system 10 in accordance with the present teachings may find application in connection with procedures for the diagnosis or treatment of a variety of tissues in human and on human bodies. Further, it should be understood that "implementing a procedure" may encompass a wide variety of actions leading to, or resulting in, diagnosis and/or treatment. Therefore, implementing a procedure may include simulating one or more actions that a clinician wants to perform (e.g., determining whether a catheter can assume a desired configuration relative to a patient's particular anatomy). Implementing a procedure may also include establishing a plan of diagnosis or treatment (e.g., identifying target locations for diagnosis and/or treatment of tissue 12, determining an order for actions in the procedure (including the order in which target locations are visited (e.g. by determining an optimal path based on the shortest distance or shortest time or most likely effectiveness of diagnosis or treatment) and identifying the preferred surgical instrument (e.g., what catheter to use based on the patient's particular anatomy)). Implementing a procedure may also include carrying out a procedure by forming diagnostic and/or therapeutic acts on body 14. System 10 may include an ablation catheter 16, a medical device position and navigation system 18, a remote catheter guidance system (RCGS) 20, a display system 22, data storage units 24, 26, and an electronic control unit (ECU) 28.

Catheter 16 is provided for examination, diagnosis and treatment of internal body tissues such as tissue 12. In accordance with one embodiment of the invention, catheter 16 comprises an ablation catheter and, more particularly, an irrigated radio-frequency (RF) ablation catheter. It should be understood, however, that catheter 16 is provided for illustration only and that system 10 could be adapted for use with a variety of catheters including, for example, electrophysiology mapping catheters and intracardiac echocardiograph (ICE) catheters, as well as for use with other types of ablation catheters including those providing different types of ablation energy (e.g., cryoablation, ultrasound, etc.). Catheter 16 is connected to a fluid source 30 having a biocompatible fluid such as saline through a pump 32 (which may comprise, for example, a fixed rate roller pump or variable volume syringe pump with a gravity feed supply from fluid source 30 as shown) for irrigation. Catheter 16 is also electrically connected to an ablation generator 34 for delivery of RF energy. Catheter 16 may include a cable connector or interface 36, a handle 38, a shaft 40 having a proximal end 42 and a distal end 44 (as used herein, "proximal" refers to a direction toward the end of the catheter near the clinician, and "distal" refers to a direction away from the clinician and (generally) inside the body of a patient) and one or more electrodes 46, 48. Catheter 16 may also include other conventional components not illustrated herein such as a temperature sensor, additional electrodes, and corresponding conductors or leads. In accordance with one embodiment of system 10, catheter 16 may further include a memory accessible upon connection to ECU 28 or another means for providing identifying information for catheter 16 (e.g., catheter manufacturer, model or type, potential configurations for catheter 16, etc.) to ECU 28.

Connector 36 provides mechanical, fluid and electrical connection(s) for cables extending from RCGS 20, pump 32, and ablation generator 34. Connector 36 is conventional in the art and is disposed at a proximal end of catheter 16.

Handle 38 provides a location for the clinician to hold catheter 16 and may further provides means for steering or guiding shaft 40 within body 14. For example, handle 38 may include means to change the length of a guidewire extending through catheter 16 to distal end 44 of shaft 40 to steer distal end 44 and, thus, shaft 40. Handle 38 is also conventional in the art and it will be understood that the construction of handle 38 may vary and may be absent in a fully-robotic implementation of the system.

Shaft 40 is an elongated, flexible member configured for movement within body 14. Shaft 40 supports electrodes 46, 48, associated conductors, and possibly additional electronics used for signal processing or conditioning. Shaft 40 may also permit transport, delivery, and/or removal of fluids (including irrigation fluids and bodily fluids), medicines, and/or surgical tools or instruments. Shaft 40 may be made from conventional materials such as polyurethane and defines one or more lumens configured to house and/or transport electrical conductors, fluids, or surgical tools. Shaft 40 may be introduced into a blood vessel or other structure within body 14 through a conventional introducer sheath. Shaft 40 may then be steered or guided through body 14 to a desired location such as tissue 12 using RCGS 20 or with guide wires or with pullwires or other means known in the art.

Electrodes 46, 48 are provided for a variety of diagnostic and therapeutic purposes including, for example, electrophysiological studies, catheter identification and location, pacing, and cardiac mapping and ablation. In the illustrated embodiment, catheter 16 includes an ablation tip electrode 46 at distal end 44 of shaft 40 and one or more ring electrodes 48. It should be understood, however, that the number, orientation, and purpose of electrodes 46, 48 may vary.

System 18 is provided to determine the position and orientation of catheter 16 and similar devices within body 14. System 18 may comprise the system offered for sale under the trademark "ENSITE NAVX" by St. Jude Medical, Inc. and described in U.S. Pat. No. 7,263,397 titled "Method and Apparatus for Catheter Navigation and Location Mapping in the Heart," the entire disclosure of which is incorporated herein by reference. The system is based on the principle that when low amplitude electrical signals are passed through the thorax, body 14 acts as a voltage divider (or potentiometer or rheostat) such that the electrical potential or field strength measured at an electrode on device 16 may be used to determine the position of the electrode, and therefore device 16, relative to a pair of external patch electrodes using Ohm's law and the relative location of a reference electrode (e.g. in the coronary sinus). In one configuration, the system includes three pairs of patch electrodes that are placed on opposed surfaces of the body (e.g., chest and back, left and right sides of the thorax, and neck and leg) and form generally orthogonal x, y, and z axes as well as a reference electrode/patch that is typically placed near the stomach and provides a reference value and acts as the origin of the coordinate system for the navigation system. Sinusoidal currents are driven through each pair of patch electrodes and voltage measurements for one or more position sensors (e.g., electrodes) associated with the medical device are obtained. The measured voltages are a function of the distance of the position sensors from the patch electrodes. The measured voltages are compared to the potential at the reference electrode and a position of the position sensors within the coordinate system of the navigation system is determined. In accordance with this exemplary system, system 18 may include patch electrodes 50 (namely $50_{X1}$, $50_{X2}$, $50_{Y1}$, $50_{Y2}$, $50_{Z1}$, $50_{Z2}$) a switch 52, and a signal generator 54.

Patch electrodes 50 are provided to generate electrical signals used in determining the position of catheter 16 within a three dimensional coordinate system 56 of system 18. Electrodes 50 may also be used to generate EP data regarding tissue 12. Electrodes 50 are placed orthogonally on the surface of body 14 and are used to create axes specific electric fields within body 14. Electrodes $50_{X1}$, $50_{X2}$ may be placed along a first (x) axis. Similarly, electrodes $50_{Y1}$, $50_{Y2}$ may be placed along a second (y) axis, and electrodes $50_{Z1}$, $50_{Z2}$ may be placed along a third (z) axis. Each of the electrodes 50 may be coupled to multiplex switch 52. ECU 28 is configured through appropriate software to provide control signals to switch 52 and thereby sequentially couple pairs of electrodes 50 to signal generator 54. Excitation of each pair of electrodes 50 generates an electromagnetic field within body 14 and within an area of interest such as the heart. Voltage levels at non-excited electrodes 50 may be filtered and converted and provided to ECU 28 for use as reference values.

In an alternative embodiment, system 18 may comprise a system that employs magnetic fields to detect the position of catheter 16 within body 14 such as the system offered for sale under the trademark "GMPS" by MediGuide, Ltd. and generally shown and described in, for example, U.S. Pat. No. 7,386,339 entitled "Medical Imaging and Navigation System," the entire disclosure of which is incorporated herein by reference. In such a system, a magnetic field generator may be employed having three orthogonally arranged coils, arranged to create a magnetic field within body 14 and to control the strength, orientation, and frequency of the field. The magnetic field generator may be located above or below the patient (e.g., under a patient table) or in another appropriate location. Magnetic fields are generated by the coils and current or voltage measurements for one or more position sensors (e.g., a coil) associated with catheter 16 are obtained. The measured currents or voltages are proportional to the distance of the sensors from the coils thereby allowing a position of the sensors within the coordinate system 56 of system 18.

Figure 2:
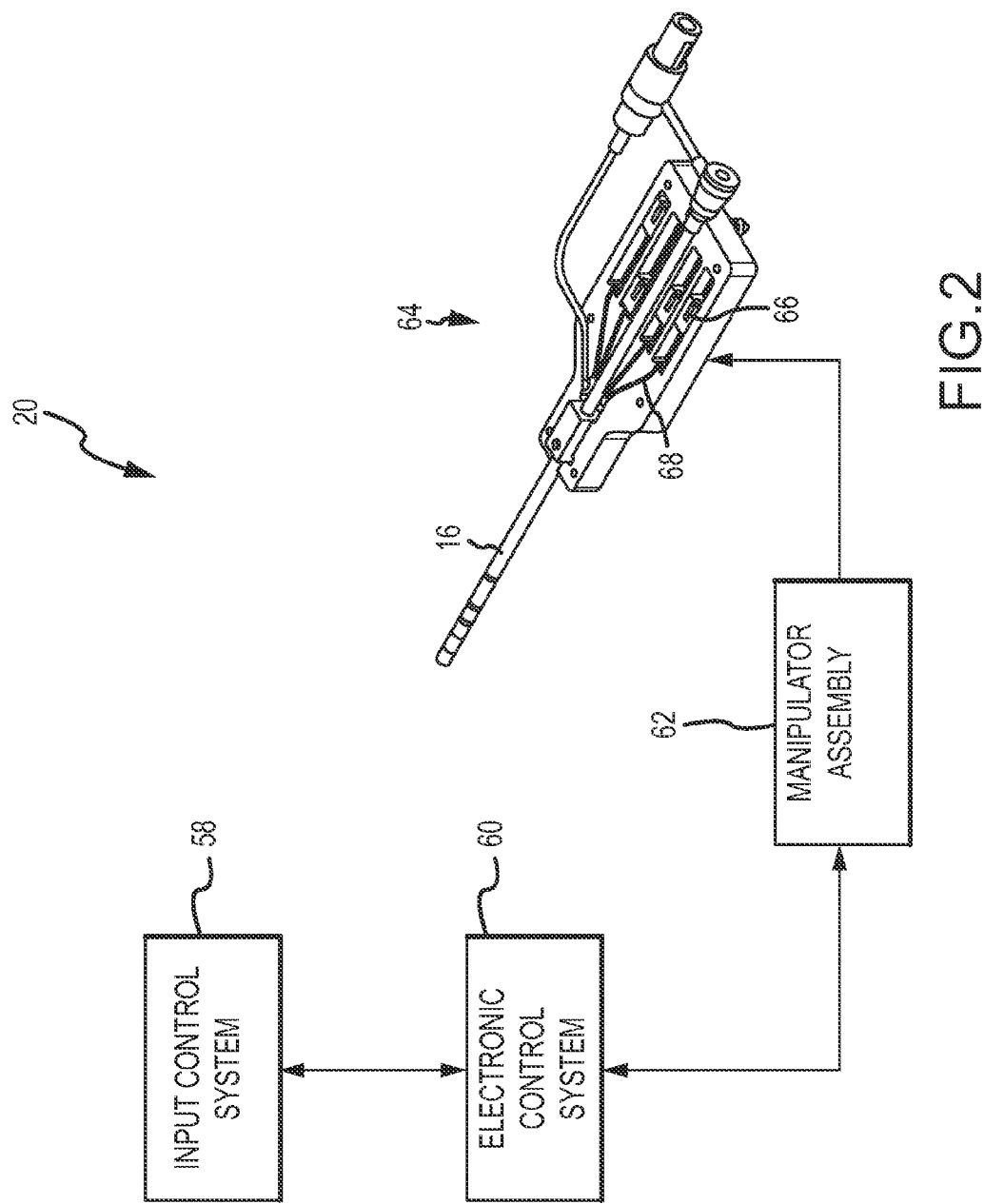
FIG. 2 is a diagrammatic view of a remote catheter guidance system for use in the system of FIG. 1.

RCGS 20 is provided to manipulate catheter 16. In particular, RCGS 20 permits control of translation, distal bending, and virtual rotation of catheter 16 and any surrounding sheath. RCGS 20 therefore provides the user with a type of control similar to that provided by conventional manually-operated systems, but allows for repeatable, precise, and dynamic movements. A clinician may identify target locations (potentially forming a path) on an image of tissue 12. RCGS 20 relates these digitally selected points to positions within the patient's actual/physical anatomy, and may thereafter command control the movement of catheter 16 to the defined positions where the clinician or the RCGS 20 can perform the desired diagnostic of therapeutic function. Referring to FIG. 2, RCGS 20 may include an input control system 58, an electronic control system 60, and a manipulator assembly 62 for operating a device cartridge 64.

Input control system 58 is provided to allow the clinician to interact with the RCGS 20 to control movement of catheter 16. System 58 may include, for example, instrumented traditional catheter handle controls, oversized catheter models, instrumented user-wearable gloves, touch screen display monitors, 2-D input devices, 3-D input devices, spatially detected styluses, and traditional joysticks. These input devices may be configured to directly control the movement of catheter 16 and any surrounding sheath, or may be configured, for example, to manipulate a target or cursor on an associated display.

Electronic control system 60 is configured to translate (i.e., interpret) inputs (e.g., motions) of the user at an input device or from another source into a resulting movement of catheter 16. The electronic control system 60 issues commands to manipulator assembly 62 (i.e., to the actuation units—electric motors) to move or bend catheter 16 to prescribed positions and/or in prescribed ways, all in accordance with the received user input and a predetermined programmed operating strategy. System 60 may include one or more stand-alone microprocessors or application specific integrated circuits (ASICs). Alternatively, system 60 may form a part of ECU 28.

Manipulator assembly 62 is configured to maneuver catheter 16 in response to commands from electronic control system 60. Assembly 62 may cause translational movement such as advancement or withdrawal of catheter 16 and effect deflection of distal end 44 of catheter 16 and/or rotation or virtual motion. Assembly 62 may include conventional actuation mechanisms (e.g., a plurality of electric motor and lead screw combinations) for linearly actuating one or more control members (e.g., steering wires) associated with catheter 16 for achieving the above-described translation, deflection, and/or rotation (or virtual rotation).

Device cartridge 64 is provided to translate movement of elements in manipulator assembly 62 to catheter 16. Cartridge 64 receives and retains proximal end 42 of catheter 16. Cartridge 64 may include sliding blocks 66 each coupled to a corresponding steering wire 68 so as to permit independent tensioning of each wire 68. Movement of the blocks 66 is controlled by manipulator assembly 62 to cause tensioning of the wires 68 and thereby affect translation, deflection, and rotation of catheter 16.

A more complete description of various elements of an RCGS may be found in the following patent applications that are incorporated herein by reference: U.S. patent application Ser. No. 12/933,063 filed Sep. 16, 2010 and titled "Robotic Catheter System Input Device"; U.S. patent application Ser. No. 12/751,843 filed Mar. 31, 2010 and titled "Robotic Catheter System"; U.S. patent application Ser. No. 12/347,842 filed Dec. 13, 2008 and titled "Robotic Catheter Rotatable Device Cartridge"; U.S. patent application Ser. No. 12/347,826 filed Dec. 31, 2008 and titled "Robotic Catheter Manipulator Assembly"; U.S. patent application Ser. No. 12/347,811 filed Dec. 31, 2008 and titled "Robotic Catheter System"; U.S. patent application Ser. No. 12/347,442 filed Dec. 31, 2008 and titled "Model Catheter Input Device" and International Patent Application No. PCT/US2009/038597 filed Mar. 29, 2009 and titled "Robotic Catheter System With Dynamic Response" (published as WO 2009/120982).

Display system 22 is provided to convey information to a clinician to assist in diagnosis and treatment. Display system 22 may comprise one or more conventional computer monitors or other display devices. Display system 22 presents a graphical user interface (GUI) to the clinician. The GUI may include a variety of information including, for example, an image of the geometry of tissue 12, electrophysiology data associated with the tissue 12, graphs illustrating voltage levels over time for various electrodes 46, 48, and images of catheter 16 and other medical devices and related information indicative of the position of catheter 16 and other devices relative to the tissue 12. In accordance with the present teachings, the GUI provides a means for the clinician to establish the configuration of distal end 44 of catheter 16 at various target locations on tissue 12.

Data storage unit 24 provides a means for storing data and particularly image data. Unit 24 may comprise a conventional memory such as a hard drive accessible by ECU 28 or portable storage in the form of a flash drive, a compact disc (CD), or a floppy disk. Unit 24 may be used as part of a structured database or data structure for the storage of data. Unit 24 may be located locally or accessed remotely over a telecommunications network (not shown) and may provide temporary or permanent storage for data. In accordance with the illustrated embodiment of system 10, unit 24 stores image data used to generate an image 70 (see FIGS. 3 and 4) of tissue 12. Image 70 may comprise, for example, a fluoroscopic image, a computed tomography (CT) image, a magnetic resonance (MR) image, an ultrasound image, and/or a rendered model or some combination of the foregoing. Image 70 may be two-dimensional or three-dimensional.

Data storage unit 26 provides a means for storing data and particularly data regarding various catheters useable with system 10 such as catheter 16. Unit 26 may comprise a conventional memory such as a hard drive accessible by ECU 28 or portable storage in the form of a flash drive, a compact disc, or a floppy disk. Unit 26 may be used as part of a structured database or data structure for the storage of data. Unit 26 may be located locally or accessed remotely over a telecommunications network (not shown) and may provide temporary or permanent storage for data. In accordance with the present teachings, the data stored in unit 26 includes information regarding potential configurations for catheter 16 and particularly distal end 44 of catheter 16.

ECU 28 provides a means for controlling the operation of various components of system 10 including catheter 16, ablation generator 34, and switch 52 of position and navigation system 18. ECU 28 also provides a means for determining the geometry of tissue 12, electrophysiology characteristics of tissue 12 and the position and orientation of catheter 16 relative to tissue 12. ECU 28 also provides a means for generating display signals used to control display 22. ECU 28 may comprise one or more programmable microprocessors or microcontrollers or may comprise one or more ASICs. ECU 28 may include a central processing unit (CPU) and an input/output (I/O) interface through which ECU 28 may receive a plurality of input signals including signals generated by ablation generator 34, electrodes 46, 48 on catheter 16, patch electrodes 50 of system 18, and input control system 58 of RCGS 20 and generate a plurality of output signals including those used to control and/or provide data to catheter 16, display 22, ablation generator 34, switch 52 of system 18, and manipulator assembly 62 of RCGS 20.

Figure 3:
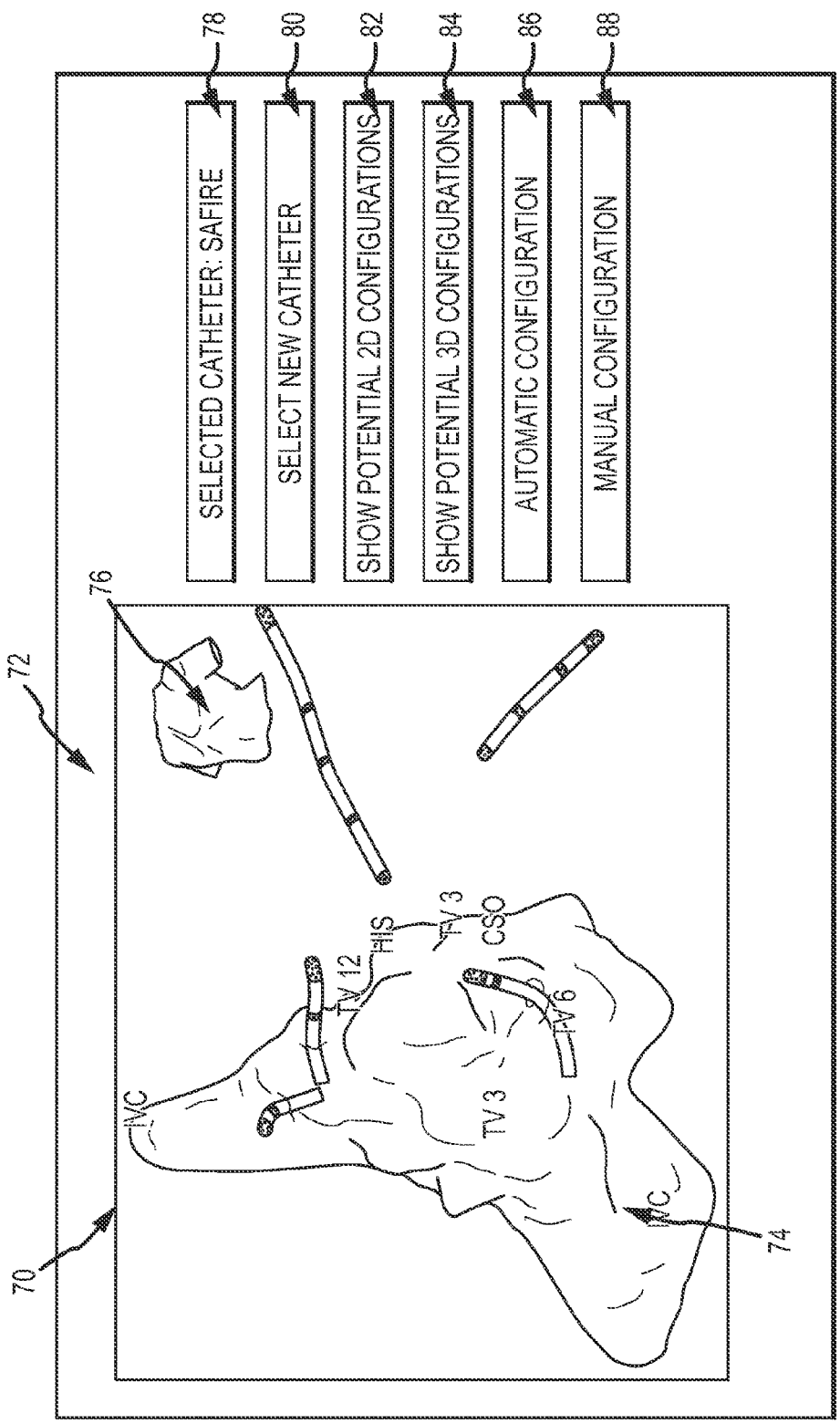
FIGS. 3-5 are diagrammatic representation of a graphical user interface generated by the system of FIG. 1.
Figure 4:
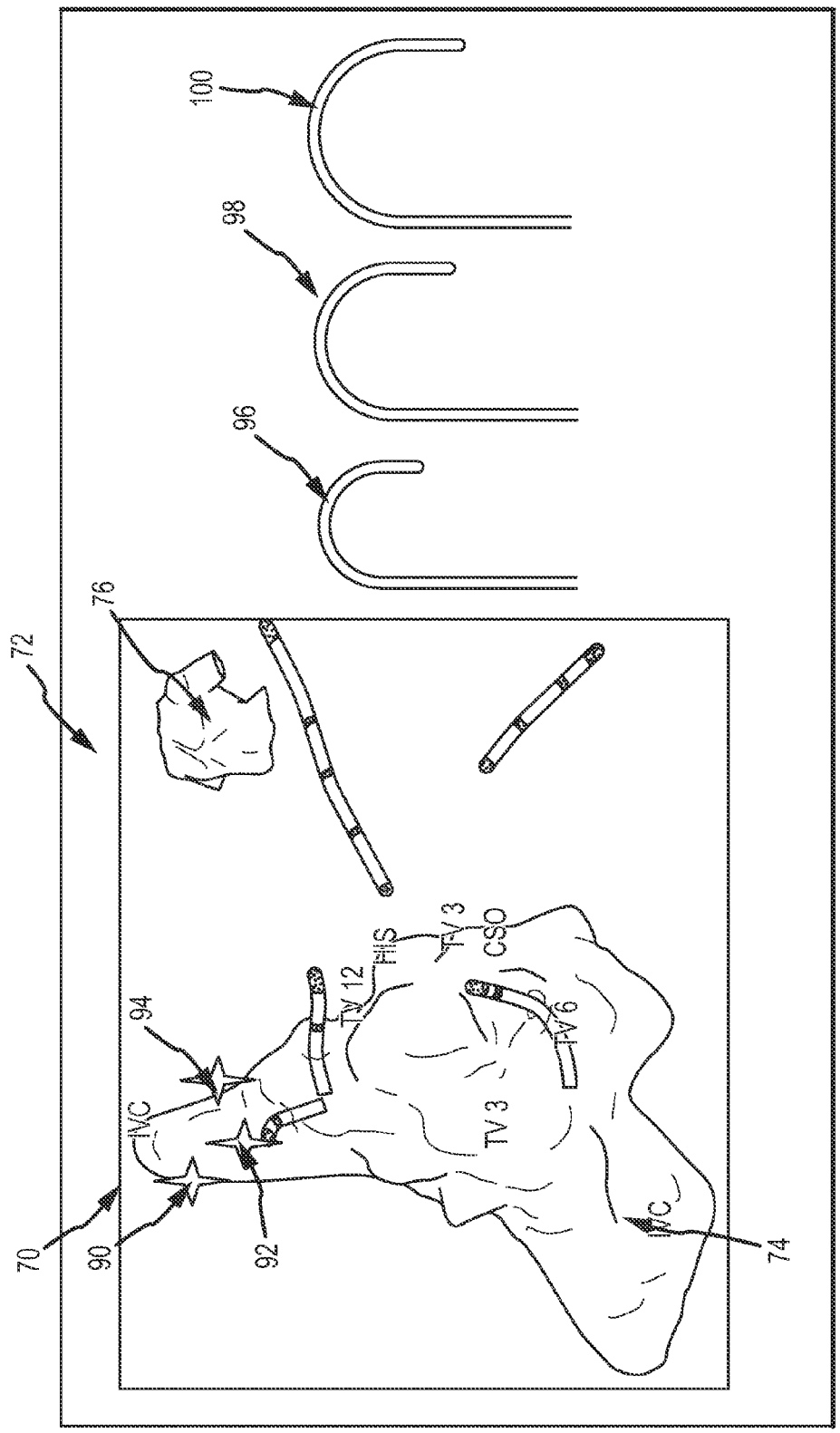

In accordance with the present teachings, ECU 28 may be configured with programming instructions from a computer program (i.e., software) to implement a procedure for the diagnosis or treatment of tissue 12 in body 14. Referring to FIGS. 3 and 4, ECU 28 may be configured to generate a GUI 72 on one or more displays in display system 22. The GUI 72 includes image 70 of tissue 12. Image 70 is preferably registered within coordinate system 56 of system 18 to allow precise identification on image 70 of target locations for diagnosis and treatment as well as subsequent guidance of catheter 16 to the identified locations. Registration of image 70 may be accomplished in a variety of ways conventional in the art including, for example, by the use of position sensors affixed to elements of the imaging system capturing the image data or through the use of fiducial markers captured in the image plane. As noted above, ECU 28 may generate image 70 with image data from data storage unit 24. In the illustrated embodiment, image 70 depicts a three dimensional model 74 of a portion of the heart and tissue 12. Image 70 further depicts a torso 76 for positional reference for the clinician and the distal ends of one or more catheters such as distal end 44 of catheter 16. GUI 72 further includes a plurality of interface features or icons such as buttons 78, 80, 82, 84, 86, 88 through which the clinician can provide inputs to system 10 or receive outputs from system 10 as described in greater detail hereinbelow. The "buttons" may be physical buttons or software implemented buttons.

ECU 28 may further be configured to identify a catheter for use in the diagnostic or therapeutic procedure. In accordance with one embodiment of system 10, ECU 28 is configured to receive identifying information from catheter 16 upon connection of catheter 16 to ECU 28. Catheter 16 may include a memory or other means for providing information regarding catheter 16 to ECU 28. This information may include, for example, the manufacturer of catheter 16, the type of catheter and the specific model. In an alternative embodiment of system 10, ECU 28 is configured to receive an input through an input device connected to ECU 28 such as GUI 72. Referring again to FIG. 3, button 80 may be used by a clinician—either directly as a touch screen input or indirectly by moving a cursor or other icon to actuate button 80 using a conventional input/output device such as a mouse or keyboard—to access a list (e.g., a menu) from which the clinician can identify the specific catheter to be used in the procedure. Button 78 displays the currently selected catheter in the illustrated embodiment. ECU 28 may use information on the identity of catheter 16 to extract data specific to catheter 16 from data storage unit 26.

ECU 28 may further be configured to receive inputs regarding target locations on tissue 12 for diagnosis or treatment. ECU 28 may receive such inputs using conventional input devices such as a mouse, keyboard, joystick, touch screen, etc. Using one of these input devices, a clinician identifies target locations on image 70 such as target locations 90, 92, 94 on FIG. 4. ECU 28 then converts the identified locations into position coordinates within coordinate system 56. ECU 28 may also generate a representation of the target locations 90, 92, 94 on image 70.

In accordance with one aspect of the present teachings, ECU 28 is further configured to determine a configuration for distal end 44 of catheter 16 at each of target locations 90, 92, 94. As used herein, "configuration" refers to the shape and/or orientation of distal end 44 of catheter 16 to be able to effect the desired diagnosis or therapy at a particular target location (e.g., 90, 92, or 94). Referring now to FIG. 4, in one embodiment of system 10, ECU 28 determines the configuration of distal end 44 based on a selection by the clinician from among one or more potential configurations for distal end 44 of catheter 16. ECU 28 is configured to generate a plurality of potential configurations for distal end 44 of catheter 16 and, with reference to FIG. 4, to display a plurality of icons, such as icons 96, 98, 100, on GUI 72 with each icon corresponding to one of the potential configurations. ECU 28 generates the potential configurations based on the identity of catheter 16 and data obtained from catheter 16 and/or data storage unit 26 regarding the possible shapes and orientations which distal end 44 of catheter 16 may assume. ECU 28 may vary a common visual characteristic such as size, color, or intensity, of icons 96, 98, 100 responsive to characteristics associated with catheter 16 or tissue 12. For example, ECU 28 may vary the color of icons 96, 98, 100 to indicate the level of strain on catheter 16 while assuming the corresponding configuration, the level of clinician skill required to achieve the corresponding configuration or the potential for achieving the corresponding configuration at the target location in view of the patient's anatomy. As a result, the clinician is able to reduce the time required to perform the procedure by eliminating impractical approaches during the planning process. Icons 96, 98, 100 may comprise two dimensional or three dimensional images of distal portion 44 of catheter 16. Referring to FIG. 3, buttons 82, 84 may be used in one embodiment to allow the clinician to select the display of two-dimensional or three-dimensional icons. Depending on various system parameters including, for example, display screen size, the number of potential configurations, etc., GUI 72 may display all available potential configurations or a subset thereof. ECU 28 is further configured, following display of icons 96, 98, 100, to recognize a selected configuration by the clinician as the configuration for a given target location 90, 92, 94 responsive to an input from the clinician.

In accordance with another embodiment of system 10, ECU 28 determines the configuration of distal end 44 of catheter 16 by automatically selecting the configuration from among a plurality of potential configurations as opposed to relying on clinician input or selection. ECU 28 may, for example, select the configuration responsive to a characteristic associate with tissue 12. Based on the stored knowledge of the physical anatomy of the tissue 12, ECU 28 may determine the best configuration for diagnosis or treatment to account for tissue shape and surrounding structures. Referring to FIG. 3, GUI 72 may allow a clinician to direct ECU 28 to make the selection using button 86.

Figure 5:
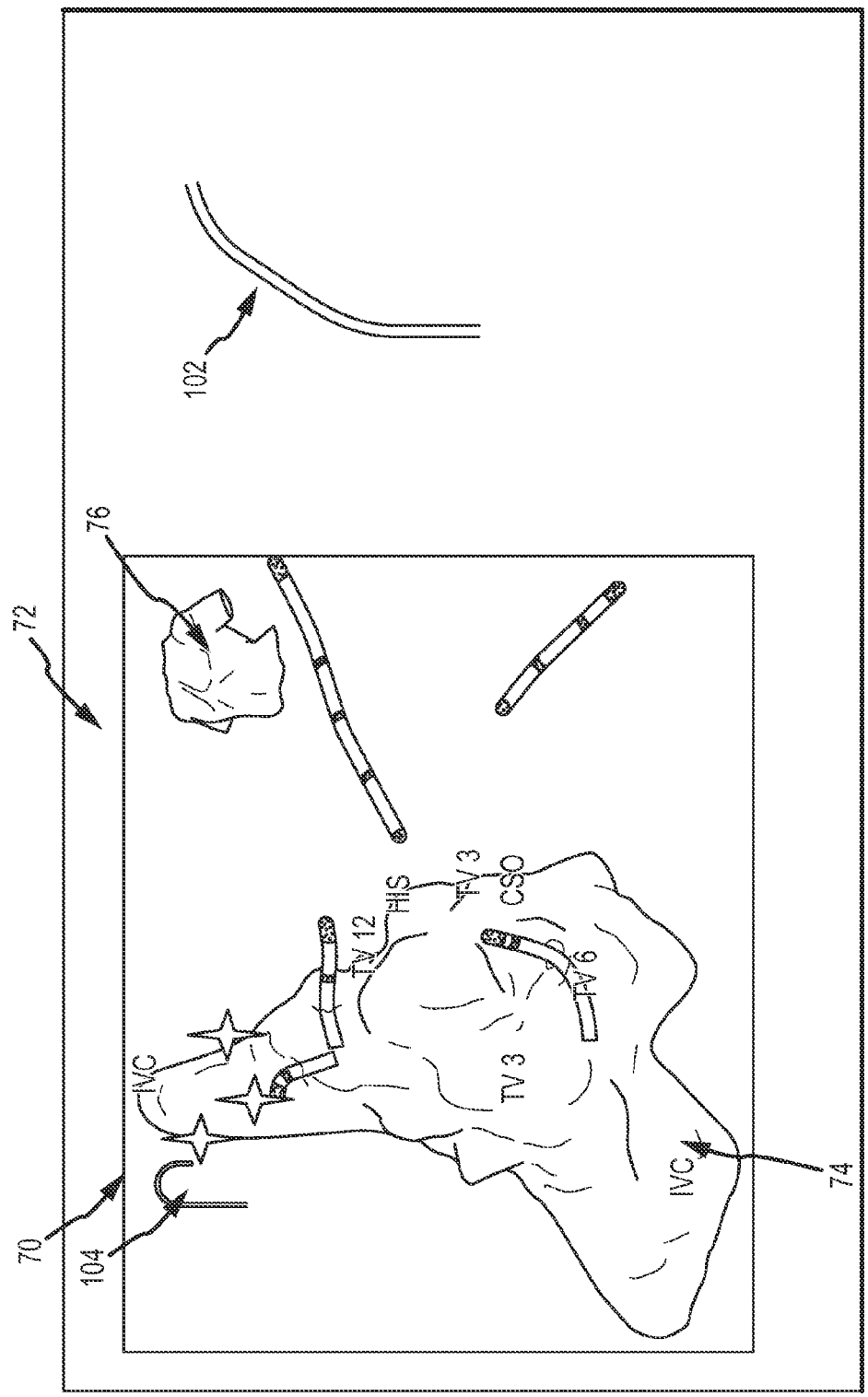

In accordance with yet another embodiment of system 10, ECU 28 determines the configuration of distal end 44 of catheter 16 responsive to manual configuration by the clinician (as opposed to selecting from among potential configurations). Referring to FIG. 3, the clinician may select this option using button 88. Referring to FIG. 5, ECU 28 may cause GUI 72 to display an icon 102 representing distal end 44 of catheter 16—possibly with a handle (not shown) for adjusting the configuration shown in icon 102. Using a conventional input device such as a mouse or touch screen, the clinician can adjust the shape and/or orientation of the distal end 44 of catheter 16 shown in icon 102.

In the embodiments in which the clinician provides input to ECU 28 to determine the configuration of distal end 44 of catheter 16 (i.e., where the clinician selects from among potential configurations generated by ECU 28 or manually configures the distal end 44 of catheter 16 on GUI 72), ECU 28 may be further configured to warn the clinician if the chosen configuration cannot be implemented. In particular, ECU 28 may be configured to determine whether the chosen configuration matches a potential configuration for distal end 44 of catheter 16. This determination may be based on characteristics associated with the catheter 16 or tissue 12. For example, ECU 28 may determine that it is not possible to place distal end 44 into a manual configuration selected by the clinician based on structural characteristics of catheter 16. Alternatively, ECU 28 may determine that it is not possible to place distal end 44 into a selected configuration at a particular target location 90, 92, 94 based on the patient's anatomy. ECU 28 may be further configured to generate an alert if the configuration chosen by the clinician does not match a potential configuration as determined by ECU 28. This alert may comprise a visual, audio, or tactile alert to the clinician. For example, ECU 28 may modify a visual characteristic of icon 102 if ECU 28 determines it is not possible to implement the desired configuration.

Referring again to FIG. 5, ECU 28 may be further configured to superimpose a representation 104 of distal end 44 of catheter 16 on image 70 at each target location 90, 92, 94 having the configuration previously determined by ECU 28 (using any of the above described processes) for the target location 90, 92, 94. Where the configuration is determined through clinician input (i.e. by selecting among potential configurations or by manually creating a configuration), the clinician may drag the determined configuration across GUI 72 to place the configuration at one of target locations 90, 92, 94 using a mouse or touch screen input for example where ECU 28 will superimpose the representation 104 on image 70. By illustrating the configuration of distal end 44 of catheter 16 at target locations 90, 92, 94, the clinician is presented with a visual representation and confirmation of the intended configuration. As a result, the clinician is better able to plan the order of the procedure to optimize diagnosis or treatment. The clinician may, for example, set an order of diagnosis or treatment at locations 90, 92, 94 based on ease of access, the likelihood of achieving certain diagnostic or therapeutic goals, or to limit the extent of reshaping or reorienting the distal end 44 of catheter 16.

Where the configuration is determined through clinician input (i.e. by selecting among potential configurations or by manually creating a configuration), ECU 28 may also be configured to adjust the determined configuration to fit, or better fit, the shape of tissue 12. Accordingly, ECU 28 may superimpose an adjusted configuration that conforms to tissue 12. The adjusted configuration may be further adjusted by the clinician, but may be limited by established parameters or thresholds determined by ECU 28.

In accordance with another embodiment of system 10, movement of catheter 16 to and between target locations 90, 92, 94 and/or the configuration of distal end 44 of catheter 16 at each target location 90, 92, 94 is controlled by ECU 28 using RCGS 20. ECU 28 may be configured to select a location among target locations 90, 92, 94 and to generate control signals to guide the distal end 44 of catheter 16 to the selected location and to assume the determined configuration for that location. Once all of the target locations 90 92, 94 are identified, ECU 28 may determine an optimal path for moving to and between locations 90, 92, 94. ECU 28 may formulate the path based on one or more goals including, for example, the shortest overall procedure time, the shortest time to move between each target location and the next target location, the shortest path between each target location and the next target location, or the most effective path (in the case of cardiac ablation, for example, by targeting ablation energy to target locations that are most likely to correct the arrhythmia such that the procedure can be terminated before treating all target locations if treatment at initial locations is effective to relieve the arrhythmia). Once the path is determined, ECU 28 generates control signals to cause RCGS 20 (and particularly manipulator assembly 62) to move catheter 16 to and among target locations 90, 92, 94 in accordance with the determined path and may also cause distal end 44 of catheter 16 to assume the determined configuration at each target location 90, 92, 94. Alternatively, the clinician may move catheter 16 among target locations 90, 92, 94 with ECU 28 controlling only the configuration of distal end 44 of catheter 16 at each target location 90, 92, 94.

A system 10 for implementing a procedure for diagnosis or treatment of tissue in a body in accordance with the present teachings is advantageous because it permits a clinician to establish the configuration for the distal end 44 of the catheter 16 at each target location 90, 92, 94 during planning for the procedure and to evaluate potential configurations relative to limitations in the patient's anatomy or in the catheter 16 itself prior to inserting the catheter 16 into the patient's body 14. The invention also allows for optimal ordering of actions in the procedure by the physician or the system 10 itself. As a result, the time required to implement the procedure is minimized thereby reducing risks to the patient and resources required from health care providers.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for implementing a procedure for the diagnosis or treatment of tissue in a body, comprising:
    an electronic control unit configured to:
        generate a graphical user interface on a display, said graphical user interface depicting an image of said tissue;
        receive a first input regarding a first target location on said tissue;
        identify a catheter for use in said procedure;
        determine a first configuration for a distal end of said catheter at said first target location, said first configuration chosen from among a plurality of potential configurations for said distal end of said catheter, each of said plurality of potential configurations based on a structural characteristic of said catheter; and
        superimpose a first representation of said distal end of said catheter on said image of said tissue at said first target location, wherein said first representation depicts said distal end of said catheter in said first configuration.

2. The system of claim 1 wherein said electronic control unit is further configured to generate control signals to guide said distal end of said catheter to said first location and to assume said first configuration at said first location.

3. The system of claim 1 wherein said electronic control unit is further configured to:
    receive a second input regarding a second target location of said tissue;
    determine a second configuration for said distal end of said catheter at said second target location; and
    superimpose a second representation of said distal end of said catheter on said image of said tissue at said second target location, wherein said second representation depicts said distal end of said catheter in said second configuration.

4. The system of claim 3 wherein said electronic control unit is further configured to:
    select one location of said first and second target locations; and
    generate control signals to guide said distal end of said catheter to said one location of said first and second target locations and to assume a corresponding one of said first and second configurations at said one location.

5. The system of claim 4 wherein said electronic control unit is further configured to generate control signals to guide said distal end of said catheter to another location of said first and second target locations and to assume a corresponding one of said first and second configurations at said another location.

6. The system of claim 3 wherein said electronic control unit is further configured to suggest an order of said first and second target locations for diagnosis or treatment.

7. The system of claim 1 wherein said electronic control unit is further configured, in identifying said catheter, to receive identifying information from said catheter upon connection of said catheter to said electronic control unit.

8. The system of claim 1 wherein said electronic control unit is further configured, in identifying said catheter, to receive a second input through an input device connected to said electronic control unit.

9. The system of claim 1 wherein said electronic control unit is further configured, in determining said first configuration, to:
    generate said plurality of potential configurations for said distal end of said catheter;
    display a plurality of icons on said graphical user interface, each icon of said plurality of icons corresponding to a potential configuration in at least a subset of said plurality of potential configurations; and
    recognize a selected configuration from among said plurality of potential configurations as said first configuration responsive to a second input.

10. The system of claim 9 wherein a value for a visual characteristic associated with each of said plurality of icons varies responsive to a characteristic associated with one of said catheter and said tissue.

11. The system of claim 1 wherein said electronic control unit is further configured, in determining said first configuration, to select said first configuration from among said plurality of potential configurations for said distal end of said catheter.

12. The system of claim 11 wherein said electronic control unit selects said first configuration responsive to a characteristic associated with said tissue.

13. The system of claim 1 wherein said electronic control unit is further configured to generate an alert if said first configuration cannot be implemented at said first target location.

14. An article of manufacture, comprising:
    a computer storage medium having a computer program encoded thereon for implementing a procedure for the diagnosis or treatment of tissue in a body, said computer program including code for:
        generating a graphical user interface on a display, said graphical user interface depicting an image of said tissue;
        receiving a first input regarding a first target location on said tissue;
        identifying a catheter for use in said procedure;
        determining a first configuration for a distal end of said catheter at said first target location, said first configuration chosen from among a plurality of potential configurations for said distal end of said catheter, each of said plurality of potential configurations based on a structural characteristic of said catheter; and
        superimposing a first representation of said distal end of said catheter on said image of said tissue at said first target location wherein said first representation depicts said distal end of said catheter in said first configuration.

15. The article of manufacture of claim 14 wherein said computer program includes code for generating control signals to guide said distal end of said catheter to said first location and to assume said first configuration at said first location.

16. The article of manufacture of claim 14 wherein said computer program includes code for:
receiving a second input regarding a second target location of said tissue;
determining a second configuration for said distal end of said catheter at said second target location;
superimposing a second representation of said distal end of said catheter on said image of said tissue at said second target location, wherein said second representation depicts said distal end of said catheter in said second configuration;
selecting one location of said first and second target locations; and
generating control signals to guide said distal end of said catheter to said one location of said first and second target locations and to assume a corresponding one of said first and second configurations at said one location.

17. The article of manufacture of claim 16 wherein said computer program includes code for generating control signals to guide said distal end of said catheter to another location of said first and second target locations and to assume a corresponding one of said first and second configurations at said another location.

18. The article of manufacture of claim 14 wherein said code for determining said first configuration includes code for:
generating said plurality of potential configurations for said distal end of said catheter;
displaying a plurality of icons on said graphical user interface, each icon of said plurality of icons corresponding to a potential configuration in at least a subset of said plurality of potential configurations; and
recognizing a selected configuration from among said plurality of potential configurations as said first configuration responsive to a second input.

19. The article of manufacture of claim 18 wherein a value for a visual characteristic associated with each of said plurality of icons varies responsive to a characteristic associated with one of said catheter and said tissue.

20. The article of manufacture of claim 14 wherein said computer program includes code for generating an alert if said first configuration cannot be implemented at said first target location.

21. A system for implementing a procedure for the diagnosis or treatment of tissue in a body, comprising:
means for generating a graphical user interface on a display, said graphical user interface depicting an image of said tissue;
means for receiving a first input regarding a first target location on said tissue;
means for identifying a catheter for use in said procedure;
means for determining a first configuration for a distal end of said catheter at said first target location, said first configuration chosen from among a plurality of potential configurations for said distal end of said catheter, each of said plurality of potential configurations based on a structural characteristic of said catheter; and
means for superimposing a first representation of said distal end of said catheter on said image of said tissue at said first target location, wherein said first representation depicts said distal end of said catheter in said first configuration.

\* \* \* \* \*